United States Patent
Meredith et al.

[11] Patent Number: 5,392,779
[45] Date of Patent: Feb. 28, 1995

[54] TESTING IMPLANTS

[75] Inventors: Neil Meredith; Peter Cawley, both of London, Great Britain

[73] Assignee: Imperial College of Science, Technology & Medicine, London, Great Britain

[21] Appl. No.: 129,076

[22] PCT Filed: Apr. 13, 1992

[86] PCT No.: PCT/GB92/00663
§ 371 Date: Oct. 28, 1993
§ 102(e) Date: Oct. 28, 1993

[87] PCT Pub. No.: WO92/18053
PCT Pub. Date: Oct. 29, 1992

[30] Foreign Application Priority Data

Apr. 11, 1991 [GB] United Kingdom ............... 9107700

[51] Int. Cl.⁶ ............................................... A61B 8/00
[52] U.S. Cl. ................................................. 128/660.01
[58] Field of Search .................. 128/660.01, 660.02, 128/660.03, 24 AA, 774; 433/172, 173, 174; 606/99

[56] References Cited

U.S. PATENT DOCUMENTS

| | | | |
|---|---|---|---|
| 5,024,239 | 6/1991 | Rosenstein | 128/774 |
| 5,103,806 | 4/1992 | McLeod et al. | 128/24 AA |
| 5,143,072 | 9/1992 | Kantorovich et al. | 128/660.02 |
| 5,161,521 | 11/1992 | Kasahara et al. | 128/660.01 |
| 5,221,204 | 6/1993 | Kruger et al. | 433/173 |
| 5,284,484 | 2/1994 | Hood et al. | 606/99 |

*Primary Examiner*—George Manuel
*Attorney, Agent, or Firm*—Bell, Seltzer, Park & Gibson

[57] ABSTRACT

Method and apparatus for testing an implant attached to a bone of a human or animal subject includes a member releasably attached to the implant. The member carries a transducer for exciting the member with a variable frequency AC signal, and a transducer for detecting a resonance frequency of the member. The detected resonance frequency is used to assess the degree of attachment of the implant to the bone.

18 Claims, 3 Drawing Sheets

TESTING IMPLANTS

The present invention relates to a method and apparatus for testing an implant attached to a bone of a human or animal subject. The use of implants involves the insertion of a metal fixture into a prepared hole in the bone. During the healing process, the surrounding bone develops an intimate contact with the implant surface and after a suitable time a prosthesis may be attached to the fixture. Such implants are frequently used in dentistry and in cosmetic surgery.

There is a need for a means of clinically observing the quality of the union between the bone and the implant surface. Implant failures can be caused by errors in placement, and premature or inappropriate loading. A nondestructive test which could be used before loading the implant would help to reduce failures of this type, and would also enable periodic tests to be carried out on implants which are in use to ensure that they are still satisfactory. The test could also provide a quantitative comparison between different implant systems.

X-rays are sometimes used to test the condition of an implant, but they can only show the presence of gross bone loss around the implant. It is also very difficult to monitor the progress of integration over time with x-rays, since it is difficult to reproduce the viewing position and angle with sufficient accuracy. A different sort of test, albeit a crude one, is to tap the structure attached to the implant with a surgical instrument. This test can only distinguish between satisfactory implants and the most grossly defective systems.

It is therefore an object of the present invention to provide a non-destructive test which is capable of giving a reliable indication of the quality and/or extent of the union between an implant and the bone to which it is attached.

Accordingly there is provided a method of testing an implant attached to a bone of a human or animal subject, the method comprising the steps of bringing a member into contact with the implant; detecting at least one resonance frequency of the member when it is in contact with the implant; and interpreting the detected resonance frequency in terms of the degree of the attachment of the implant with respect to the bone.

The stiffness of the joint or interface between the implant and the bone, and also the exposed length of the implant, will affect the resonance frequency of the member. Hence, monitoring this resonance frequency provides a means of assessing the integrity of the joint.

Preferably, the member is releasably attached to the implant.

According to one preferred arrangement, the member comprises a cantilever beam. The implant often includes a threaded bore by means of which the prosthesis, or a pillar or post (called an abutment) intended to carry the prosthesis, is screwed to or into the implant. The abutment or an associated fixing screw also usually has a threaded bore by means of which the prosthesis is screwed to or into the abutment. The cantilever beam, conveniently, can be screwed to or into the implant, or abutment, using the associated threaded bore in the latter.

The detected resonance frequency is conveniently compared with one or more values for the resonance frequencies of the same or similar members in contact with other implants. By comparing the detected resonance frequency with values obtained on other satisfactory or less satisfactory implants, an indication of the degree of integration of the implant can be obtained. Furthermore, the same implant could be tested when it is initially inserted, and periodically thereafter, both during the healing process, when it is intended to attach the prosthesis, and thereafter, and the various resonance frequency values compared, to obtain an indication of the progress of the integration process, whether and when a prosthesis or abutment should be attached, and, subsequently, whether the condition of the implant is still satisfactory.

The resonance frequency is conveniently detected by exciting the member with an AC signal, detecting the response of the member to the AC signal, and varying the frequency of the AC signal until the detected response of the member is a maximum. Other methods of detecting the resonance frequency are equally practicable.

The invention further resides in apparatus for testing an implant attached to a bone of a human or animal subject, the apparatus comprising a member adapted to be releasably attached to the implant; and means for detecting at least one resonance frequency of the member when it is attached to the implant.

The apparatus conveniently includes means for exciting the member with an AC signal, and a transducer for detecting the response of the member to the AC signal, the arrangement being such that the frequency of the AC signal is varied, and the transducer detects when the response of the member is at a maximum. The transducer preferably comprises a piezoelectric element, and the means for exciting the member may also conveniently comprise a piezoelectric element driven by a variable frequency oscillator. The detection and/or excitation means could alternatively comprise magnetostrictive or electromagnetic devices.

The invention will now be further described, by way of example only, with reference to the accompanying drawings, in which.

Figure 1:
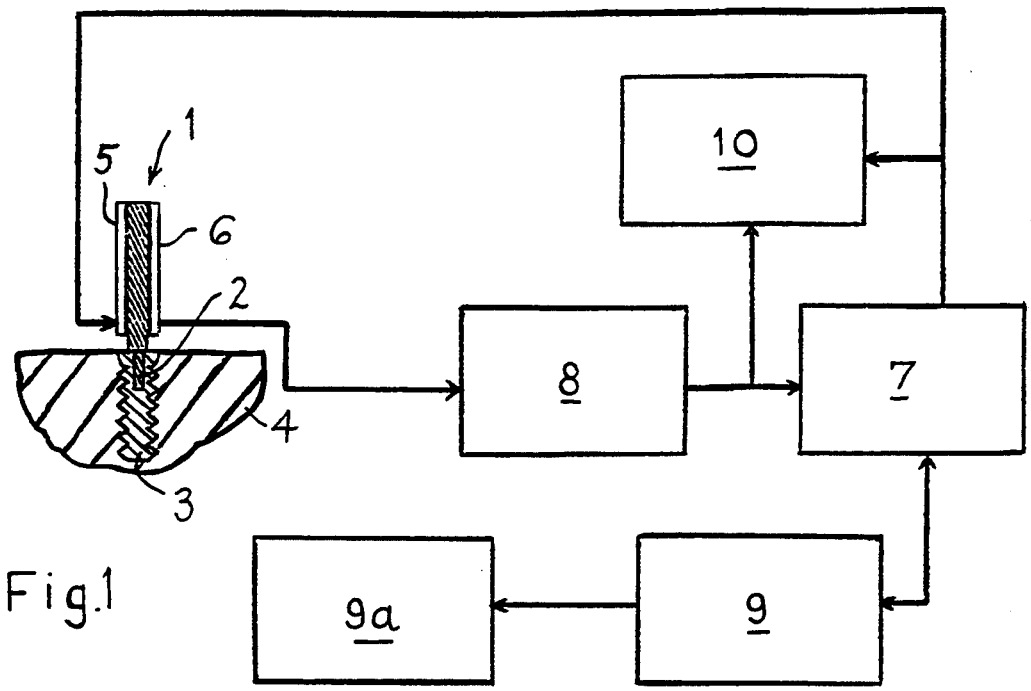
FIG. 1 is a schematic diagram of one embodiment of apparatus according to the invention.

Referring to FIG. 1, the apparatus comprises a member in the form of a cantilever beam 1 attached by means of a threaded section 2 to an implanted fixture, such as a dental implant 3, in a section of bone 4, typically a human jaw bone. The implant 3 may be any one of a number of known types, formed from a metal, such as titanium, from a ceramic material, or any other appropriate material. It may, for example, be of the type supplied by Nobelpharma in the U.K. Two transducers, such as piezoelectric elements or strain gauges 5 and 6, are attached, for example bonded, to opposite sides of the beam 1, gauge 5 being an exciter gauge and gauge 6 a receiver gauge.

The exciter gauge 5 is driven by a variable frequency oscillator, signals from which, for example in the form of a sinusoidal excitation voltage, are fed to the gauge 5 via an amplifier. The oscillator and amplifier may be incorporated in a frequency response analyser 7. Signals detected by the receiver gauge 6 are amplified by a charge amplifier 8 and applied as an input to the analyser 7. The output from the analyser, which represents the ratio of the response voltage to the excitation voltage, is fed to a processor such as a microprocessor 9, which is used to vary the frequency output of the oscillator of the analyser 7, and store the results in a data store 9a. The results may be printed out, and/or displayed on an oscilloscope 10, and/or an AC voltmeter or the like.

Figure 2:
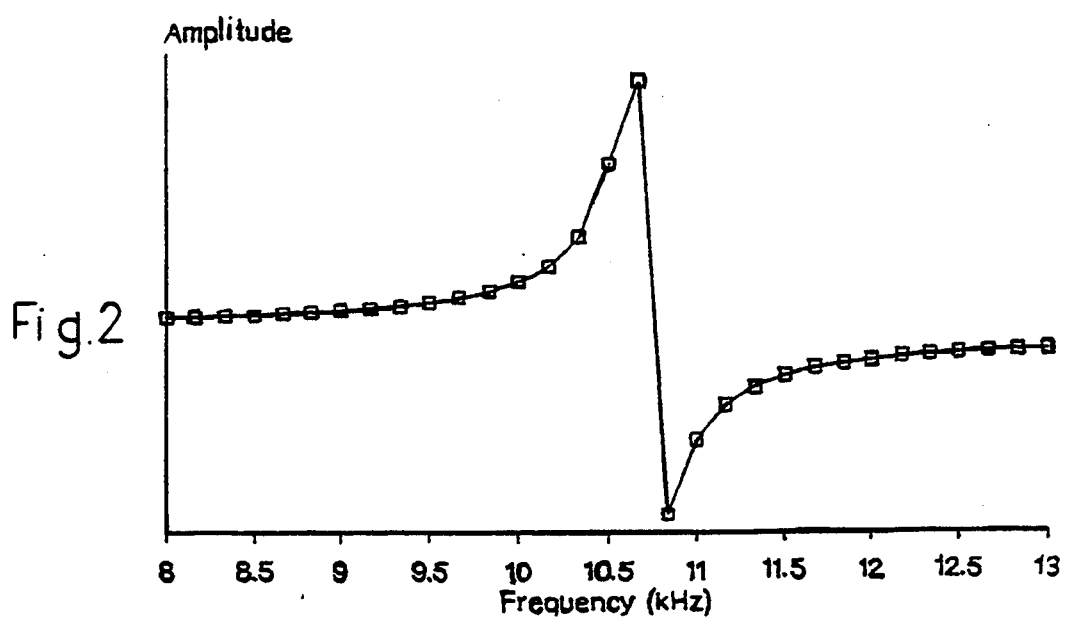
FIG. 2 is a graphical representation of a typical frequency response curve of a cantilever beam attached to a typical implant.

In use the beam 1 is secured, i.e. screwed, to the implanted implant 3 with a predetermined torque, for example using a Nobelpharma torque controller and counter tool. The variations in resonance frequency with torque have been found to be relatively small over a practical range of torques, for example of the order of 10 to 15 Ncm, so that such torque variations should not present a problem. Constant amplitude, for example 1 volt, AC excitation signals are then applied to the beam 1 via the gauge 5. The frequency of the AC excitation signals is varied until the amplitude of the signal displayed on the oscilloscope 10 is at a maximum. The resonance frequency is the frequency at which the amplitude of the ratio of the response voltage to the excitation voltage is a maximum. FIG. 2 shows the data from a coarse sweep which is used to obtain the resonance frequency roughly. A finer sweep around this region is then used to identify this frequency, typically the first or fundamental frequency, more accurately. This frequency is noted, and compared, for example, with the data for other implants at similar stages of bonding.

Figure 3:
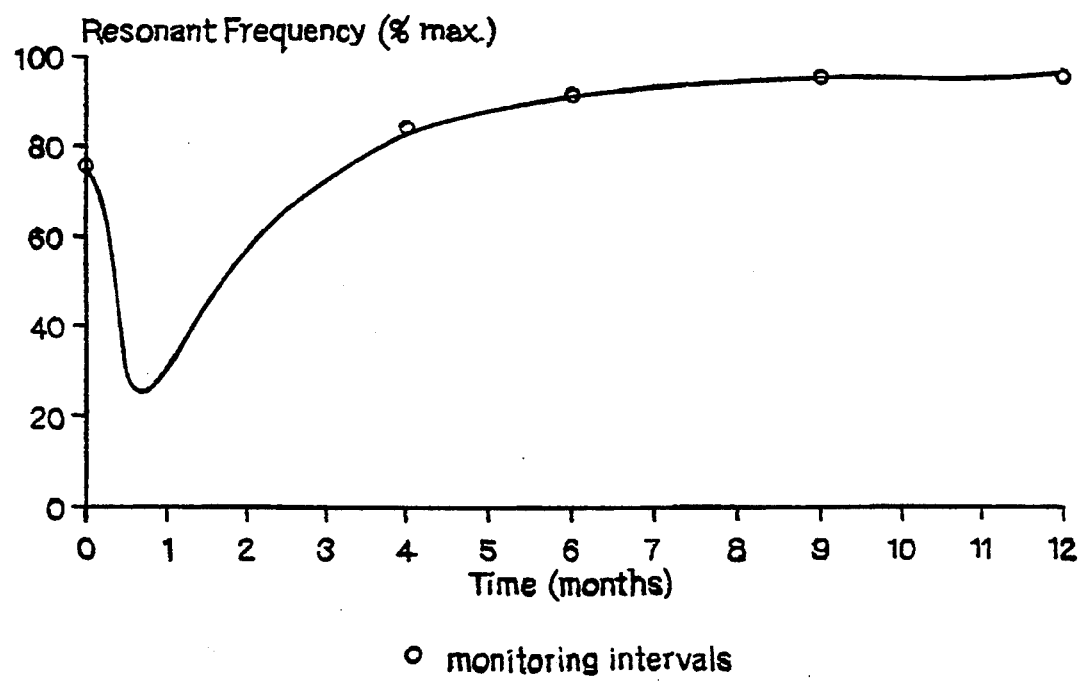
FIG. 3 is a graphical representation of the hypothetical change in the resonance frequency, over a period of time, of a cantilever beam attached to a typical implant.

It is expected that for a particular implant, the resonance frequency will vary with time as depicted in FIG. 3. Thus by comparing the detected resonance frequency with previously compiled data for similar implants, an indication of the degree of attachment of the implant can be obtained. With regard to FIG. 3, the stiffness of the interface may initially decrease following implant placement because of acute inflammatory response. The stiffness then recovers as integration occurs, and is expected eventually to approach, reach or exceed the initial value.

The technique, which is based on detection and comparison of resonance frequency shifts, rather than amplitude changes, is effective to determine the quality of the implant/tissue interface as a function of its stiffness, and also in relation to any bone loss as a function of the level or height of the marginal bone surrounding the implant.

Figure 4:
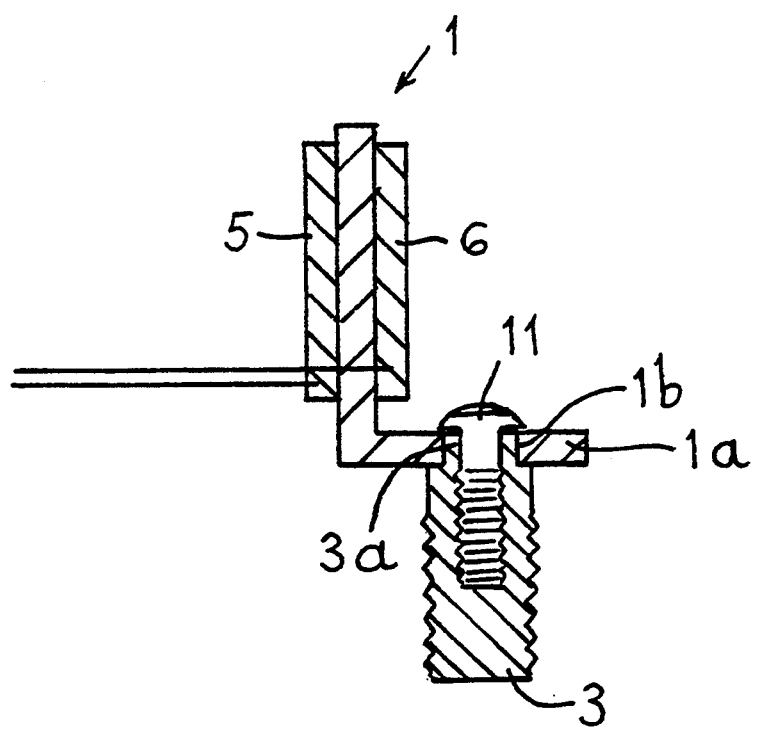
FIG. 4 is a schematic view of a second embodiment of cantilever beam.

A currently preferred cantilever beam is illustrated in FIG. 4. This beam 1 is generally L-shaped, having base limb 1a with an aperture 1b which locates over a boss 3a at the upper end of the implant 3. The beam is fixed in place by a screw 11 screwed into the threaded bore in the implant. The aperture 1b and boss 3a may be non-circular, for example hexagonal in cross-section, so that the beam orientation about the longitudinal axis of the implant may be accurately and repeatedly determined. Different readings may be obtained for different angular orientations of the beam relative to the implant, so as to determine the stiffness/bone level at different positions around the implant axis.

The beam 1 as shown in FIG. 1 or 4, which will preferably be of the same material as the implant, for example titanium, is dimensioned so as to provide a resonant frequency range of the system (placed implant and beam) of the order of 1 to 20 kH, more specifically 5 to 15 kH, and preferably in the region of about 10 kH.

For example, in the embodiment of FIG. 4, the limbs of the beam 1 may be of approximately 5 to 6 mm square crosssection, the upright limb being approximately 2 cm high, and the base limb being approximately 1.5 cm long.

It will be understood that various modifications may be made without departing from the scope of the present invention as defined in the appended claims.

For example, an additional pair of excitation/detection transducers or gauges may be mounted on the sides of the beam at 90° to the transducers or gauges 5 and 6 shown, so as to provide readings at right angles to the latter transducers, without the necessity of re-orienting the beam on the implant. Additionally, or alternatively, the beam and/or transducer system could be adapted to turn relative to the implant.

Although the beam shown in FIG. 4 is L-shaped, the upright limb could form a straight extension of the base limb 1a so as to lie generally parallel to the jaw or mandible.

In practice, the prosthesis may be attached directly to the implant 3 using the threaded bore in the latter. Alternatively, the prosthesis may be indirectly attached to the implant via a separate pillar or post (called an abutment). Such an abutment has means, such as an axial screw passing completely through the abutment, which threads into the implant bore, to fix the abutment to the implant. The upper end of the screw, or the abutment, has a threaded bore for attaching the prosthesis. The beam 1 may be attached, in the manner previously described, to the upper end of the abutment. The beam may then be employed, not only to assess the integrity of the implant/bone interface, but also the integrity of abutment/implant joint.

The transducers or gauges, and optionally also the beam may be coated, for example with an air dry acrylic material, to protect the transducers during sterilization of the apparatus. The electrical connections or wires connected to the transducers are arranged or adapted to minimize their damping effect on the resonant structure. The member may take a form other than a cantilever beam, and/or the piezoelectric transducers could be replaced by other receiver/transmitter elements, for example employing sonic resonance. The beam, instead of being basically straight, could be generally U-shaped, and connected to the implant or abutment by its base. The transducers or equivalent could be mounted on the same or opposite limbs.

We claim:

1. A method of testing an implant attached to a bone of a live subject, the method comprising the steps of bringing a member into contact with the implant; detecting at least one resonance frequency of the member when it is in contact with the implant; and interpreting the detected resonance frequency in terms of the degree of attachment of the implant with respect to the bone.

2. A method according to claim 1, including the step of releasably attaching the member to the implant.

3. A method according to claim 1 or 2, wherein the member comprises a cantilever beam.

4. A method of testing an implant attached to a bone of a live subject, the method comprising the steps of releasably attaching a cantilever beam to the implant; detecting at least one resonance frequency of the beam when it is attached to the implant; and interpreting the detected resonance frequency in terms of the degree of attachment of the implant with respect to the bone.

5. A method according to claim 4, wherein the implant includes a threaded bore, and the member is a cantilever beam secured to the implant.

6. A method of testing an implant attached to a bone of a live subject, the method comprising the steps of releasably attaching a member to the implant; detecting at least one resonance frequency of the member when it is attached to the implant; and interpreting the detected resonance frequency in terms of the degree of attachment of the implant with respect to the bone by comparing the detected resonance frequency with at least one value for the resonance frequency of an equivalent member in contact with another implant.

7. A method of testing an implant attached to a bone of a live subject, the method comprising the steps of releasably attaching a member to the implant; detecting at least one resonance frequency of the member when it is attached to the implant; and interpreting the detected resonance frequency in terms of the degree of attachment of the implant with respect to the bone by comparing the detected resonance frequency with at least one other value, taken at a different time, for the resonance frequencies of an equivalent member in contact with the same implant.

8. A method of testing an implant attached to a bone of a live subject, the method comprising the steps of releasably attaching a member to the implant; exciting the member with an AC excitation signal; detecting the response of the member of the AC excitation signal; varying the frequency of the AC excitation signal until the detected response of the member is at a maximum, thereby detecting at least one resonance frequency of the member when it is attached to the implant; and interpreting the detected resonance frequency in terms of the degree of attachment of the implant with respect to the bone.

9. A method according to claim 8, including deriving an output which is the ratio of the voltage of the AC excitation signal to the voltage of a response signal corresponding to the response of the member to the AC excitation signal.

10. Apparatus for testing an implant attached to a bone of a live subject, the apparatus comprising a member adapted to be releasably attached to the implant; and means for detecting at least one resonance frequency of the member when it is attached to the implant attached to said bone.

11. Apparatus according to claim 10, wherein the member comprises a cantilever beam.

12. Apparatus for testing an implant attached to a bone of a live subject, the apparatus comprising a member adapted to be releasably attached to the implant; excitation means for exciting the member with a variable frequency AC excitation signal; and means including a transducer for detecting at least one resonance frequency of the member when it is attached to the implant attached to said bone and excited by the AC excitation signal, by detecting the response of the member to different frequencies of the AC excitation signal, to determine when the response of the member is at a maximum.

13. Apparatus according to claim 12, wherein at least one of the excitation means and detector means comprises a piezoelectric element, the excitation means being driven by a variable frequency oscillator.

14. Apparatus for testing an implant attached to a bone of a live subject, the apparatus comprising a cantilever beam adapted to be releasably attached to the implant; and means for detecting at least one resonance frequency of the beam when it is attached to the implant attached to said bone.

15. Apparatus according to claim 14, wherein the beam is a generally L-shaped beam having a base limb, means being provided to rigidly attach the base limb of the beam to an implant.

16. Apparatus as claimed in claim 14, wherein the beam is adapted to resonate at a frequency within the range of about 1 to 20 kH.

17. Apparatus as claimed in claim 14, wherein the beam is adapted to resonate within a frequency range of about 5 to 15 kH.

18. Apparatus as claimed in claim 14, wherein the beam is adapted to resonate at a frequency of the order of 10 kH.

* * * * *

UNITED STATES PATENT AND TRADEMARK OFFICE
CERTIFICATE OF CORRECTION

PATENT NO. : 5,392,779

DATED : February 28, 1995

INVENTOR(S) : Neil Meredith, Peter Cawley

It is certified that error appears in the above-identified patent and that said Letters Patent is hereby corrected as shown below:

On the title page, item [56]:

Under References Cited, please add the following:

U.S. PATENT DOCUMENTS

| | | |
|---|---|---|
| 3,872,443 | 3/1975 | Ott |
| 4,062,229 | 12/1977 | Godfrey et al. |

FOREIGN PATENT DOCUMENTS

| | | |
|---|---|---|
| 728,082 | 11/1942 | Germany |
| 2,330,368 | 6/1977 | France |
| 181,131 | 5/1986 | Europe |
| 90/06720 | 6/1990 | WIPO |
| 427,146 | 5/1991 | Europe |

Column 4, line 3, "crosssection" should be -- cross-section --.

UNITED STATES PATENT AND TRADEMARK OFFICE
CERTIFICATE OF CORRECTION

PATENT NO. : 5,392,779
DATED : February 28, 1995
INVENTOR(S) : Neil Meredith, Peter Cawley It is certified that error appears in the above-indentified patent and that said Letters Patent is hereby corrected as shown below:

Column 5, line 29, "of" (second occurrence) should be --to--.

Signed and Sealed this

Twentieth Day of June, 1995

Attest:

BRUCE LEHMAN

Attesting Officer        Commissioner of Patents and Trademarks